(12) United States Patent
Cremer

(10) Patent No.: US 6,264,985 B1
(45) Date of Patent: Jul. 24, 2001

(54) LAMINATED TABLET WITH POINTED CORE

(75) Inventor: Karsten Cremer, Bonn (DE)

(73) Assignee: LTS Lohmann Therapie-Systeme GmbH, Neuwied (DE)

( * ) Notice: Subject to any disclaimer, the term of this patent is extended or adjusted under 35 U.S.C. 154(b) by 0 days.

(21) Appl. No.: 08/810,801

(22) PCT Filed: Sep. 4, 1995

(86) PCT No.: PCT/EP95/03474

§ 371 Date: Mar. 6, 1997

§ 102(e) Date: Mar. 6, 1997

(87) PCT Pub. No.: WO96/07401

PCT Pub. Date: Mar. 14, 1996

(30) Foreign Application Priority Data

Sep. 6, 1994 (DE) ................................. 44 31 653

(51) Int. Cl.[7] .............. A61K 9/24; A61K 9/28; A61J 3/10
(52) U.S. Cl. ............ 424/473; 71/64.07; 71/64.11; 424/408; 424/472; 424/468; 424/474; 427/2.21
(58) Field of Search .................. 424/468, 464, 424/480, 408, 474, 473, 472; 128/260; 71/64.07, 64.11; 427/2.21, 272, 212

(56) References Cited

U.S. PATENT DOCUMENTS

| | | | |
|---|---|---|---|
| 3,845,770 | * 11/1974 | Theewes et al. | 128/260 |
| 3,851,648 | * 12/1974 | Brooke | 128/260 |
| 3,924,622 | 12/1975 | Brooke | 128/260 |
| 3,993,072 | * 11/1976 | Zaffaroni | 128/260 |
| 4,692,336 | * 9/1987 | Eckenhoff et al. | 424/468 |
| 4,803,076 | * 2/1989 | Ranade | 424/438 |
| 4,814,182 | * 3/1989 | Graham | 424/484 |
| 4,814,183 | * 3/1989 | Zentner | 424/485 |
| 4,816,262 | * 3/1989 | McMullen | 424/467 |
| 5,004,614 | * 4/1991 | Staniforth | 424/466 |
| 5,593,694 | * 1/1997 | Hayashida | 424/468 |

FOREIGN PATENT DOCUMENTS

| | | |
|---|---|---|
| 4 025 484 | 10/1991 | (DE) . |
| 4 341 442 | 6/1995 | (DE) . |
| 259 219 | 3/1988 | (EP) . |
| 432 607 | 6/1991 | (EP) . |
| 542 364 | 5/1993 | (EP) . |

OTHER PUBLICATIONS

Higuchi, *J. PLharm. Sci.*, vol. 50, pp. 874–875 (1961).
Theeuwes, *Pharmacy International*, vol. 5, pp. 293–296 (Dec. 1984).

* cited by examiner

*Primary Examiner*—Diana Dudash
*Assistant Examiner*—Mina Haghighatian
(74) *Attorney, Agent, or Firm*—Wenderoth, Lind & Ponack, L.L.P.

(57) ABSTRACT

A dry-coated tablet for controlled release of active substance, having an erodible core tablet (1) containing at least one active substance, and a substantially erosion-resistant shell consisting of a dry-coated layer (5), is characterized in that the dry-coated layer (5) has at least one opening (6), and one end of the core tablet (1) extends as far as the opening (6).

11 Claims, 2 Drawing Sheets

US 6,264,985 B1

LAMINATED TABLET WITH POINTED CORE

This application is § 371 application of PCT/EP95/03474.

BACKGROUND OF THE INVENTION

The invention relates to a dry-coated tablet for controlled release of active substances. The dry-coated tablet is intended to allow active substances to be released in liquid media, for example body fluids, in a delayed manner and/or with the desired rate profile.

Tablets are often used particularly for the purpose of oral administration of pharmaceutical active substances. Depending on the therapeutic objective, a distinction may in this context be made between tablets with rapid release of active substance and those with controlled release of active substance. A controlled release of active substance is sought if, for example, the active substance has a short biological half-life. In this case, administration in the form of rapid-release tablets would lead to considerable fluctuations in the active substance plasma concentrations, unless small doses were taken at short intervals. Experience shows that patients seldom comply with prescribed intake frequencies of this kind, and this leads to failure of the treatment. The intake of tablets whose active substance release is controlled in such a way that it takes place with uniform delay over a period of several hours can keep the fluctuation of the active substance plasma concentrations to a minimum, while at the same time the low frequency of intake improves patient compliance. The therapeutically required delivery of active substance is guaranteed in this way, whilst the danger represented by particularly high plasma concentration peaks is avoided.

A delayed release of active substance can be achieved in different ways. It can be accomplished, on the one hand, by physical-chemical measures to which an active substance is subjected. Such measures include, for example, the use of active substance adsorbates, sparingly soluble active substance salts and complexes.

However, a greater control over the degree of delay is generally achieved by galenic techniques. Many of the known delayed-release tablets can be assigned to the matrix systems on the one hand or the membrane systems on the other hand. Matrix systems contain active substances in dissolved and suspended form, more rarely also in the form of a multi-particle pharmaceutical intermediate. Release takes place either by diffusion of active substances from the matrix or by continuous erosion of the matrix, starting at the edge zones. Membrane systems, by contrast, comprise a reservoir containing active substance, which reservoir is covered with a coating which is semi-permeable at least for the active substance. The release in this case takes place by means of diffusion of the active substance through the membrane.

The rate of release in these systems depends on various influencing factors. In the case of matrix tablets, these factors include, inter alia, the specific properties of the auxiliaries used, such as molar weight, solubility, swellability and glass transition temperature, but also the active substance concentration and the geometric shape of the matrix. In the case of release by diffusion from a matrix, the important factors include the size of the active surface, the matrix volume, the coefficient of diffusion, the concentration and solubility of the active substance in the matrix, the porosity and tortuosity of the matrix, and the diffusion resistance between matrix and a surrounding liquid medium. Coated tablets release active substances at a rate which primarily depends on the size of the active surface, the permeability of the active substance through the membrane, and the concentration gradient on both sides of the membrane.

With conventional matrix tablets and film-coated tablets, the rate of release can be controlled only to a limited extent. The realization of a uniformly delayed release runs into difficulties in both cases. In the case of erodible matrices, the rate of release changes to a greater or lesser extent, depending on the shape of the matrix, during the course of the release, on account of the change in the erodible surface. In the case of diffusion matrices, on the other hand, a diffusion layer which grows as the active substance depletion increases is built up during the course of release, with the consequence that the rate of release decreases as a function of $t^{+hu\ 1/2}$ (Higuchi, J. Pharm. Sci. 50, p. 874, 1961).

An improved control over the release profile was achieved through the introduction of further control mechanisms. For example, EP-A 0 432 607 describes a multi-layer tablet whose matrix containing active substance represents one of the layers, which is partially covered by auxiliary layers. U.S. Pat. No. 3,924,622 describes the use of geometric elements, although the device which is claimed in the latter for controlled release of active substance is not a tablet. Nevertheless, the geometric control principle of compensatory surface enlargement is described here, by which control principle the factors slowing release—prolongation of the diffusion path, active substance depletion, etc.—are counteracted. The device is designed such that it has an active substance reservoir with a defined, constant opening through which the active substance passes outwards. The release takes place by means of erosion of the reservoir. The shape of the reservoir is chosen such that the erosion surface is continuously enlarged as the distance of the erosion front from the opening increases during the course of the release.

The devices described in EP-A 0 542 364 are based on a similar control mechanism. In these devices too, a surface, namely the diffusion front, increases in size during the course of the release. This has the same maintaining effect on the rate of release as does the geometric element in U.S. Pat. No. 3,924,622. Express mention is made of the possibility of embodiment as a tablet, the requirements in respect of the preferred design being somewhat complex.

EP-A 0 259 219 describes a coated tablet with a central opening thorough which the active substance is released outwards from the core tablet. The thickness of the core tablet increases from the central opening towards the periphery, as a result of which, analogously to the above-described systems, the distance, increasing during the course of release, between the erosion or diffusion front and the opening is compensated by a surface enlargement.

A compensation mechanism of another kind is described in unpublished German Patent Application P 43 41 442.7. This concerns a device with a matrix which contains active substance and which is initially partially covered by erodible auxiliary layers with thickness gradients, and these auxiliary layers erode during the course of the release and thereby bring about an enlargement of the matrix surface actively available for release.

A similarly effective control over the rate of release can be achieved using osmotic systems. These include a coated active substance and auxiliary substance reservoir in which an osmotic pressure builds up after admission of water. The membranes which surround the active substance reservoirs are semi-permeable; they permit the entry of water, but are impermeable to active substances, and yet have an almost microscopically small opening through which water which has diffused inwards can escape together with dissolved active substance. With such osmotic systems it was sometimes possible to achieve constant rates of release over a relatively long period (Theuwes, Pharm. Int. 5, 293, 1984).

All of these devices for controlled release of active substance have, compared to conventional delayed-release tablets of simple design, the advantage of being able to control the rate of release to a considerably greater extent. In the case of the precise osmotic systems, this is true in particular when a release of zero order is sought. The devices with geometric control elements are more variable in this respect and can also be used more suitably for achieving other release profiles.

However, compared to the conventional delayed-release tablets, many of the proposed embodiments have the disadvantage that they are very costly to produce. This is all the more so with the osmotic systems in which the conventional tabletting technology cannot as yet be used and the inclusion of an opening in the coating demands the very highest precision and reproducibility and can be accomplished only with the aid of expensive technologies and with limited manufacturing efficiency.

SUMMARY OF THE INVENTION

The invention is based on the object of making available a tablet for controlled release of active substances, which tablet has geometric elements for controlling the rate of release, namely an opening through which active substance escapes, in the process of which a diffusion or erosion front is formed which enlarges as the distance from this opening increases, but which tablet, in contrast to the prior art, can be produced simply and in large batch numbers using a conventional and highly-efficient tabletting technology.

DETAILED DESCRIPTION OF THE INVENTION

The tablet according to the invention has an inner core tablet which contains active substance, tapers or narrows at least to one end region, and is placed in the tablet in such a way that the pointed or narrow end region extends as far as the outer edge of the tablet. This arrangement has the effect that the end region of the inner core tablet extending as far as the outer edge forms an opening on the outer edge of the tablet, through which opening active substance is released. The opening is in this case chosen such that it determines the rate of release. The invention provides for the first time the possibility of providing dry-coated tablets with a defined opening, which is small in relation to the dimensions of the core, and of using them to control the rate of release, and these tablets can be produced simply, precisely and by economic means in large batch sizes using conventional and highly efficient tabletting technology.

The known control principle of surface enlargement by erosion can be effectively employed here. By means of the shape of the core tablet, which is established as a function of the requirements concerning the release profile in each individual case, it is possible to determine with which gradient the cross-sectional area relevant to release—that is to say in this case the erosion or diffusion front—increases with the distance from the opening.

The cross-sectional area of the core tablet can advantageously change continuously on the basis of a function of first or second order as its distance from the opening of the dry coat increases. However, use can also be made of the cross-sectional area of the core tablet changing discontinuously as the distance from the opening increases. A further embodiment envisages the core tablet containing at least two different active substances, for example for pretreatment and after-treatment of a medical condition, and these being present either in homogeneous mixture or in different layers of the core tablet.

Figure 1:
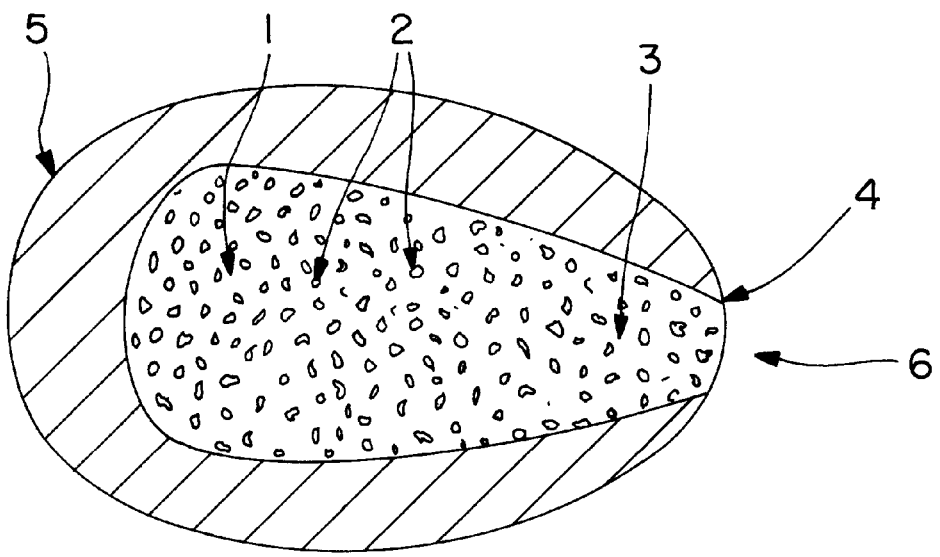
FIGS. 1, 3, and 4 illustrate tablets according to the present invention.

FIG. 1 shows the structure of a tablet according to the invention. The core tablet (1), which contains active substance (2), is designed tapering towards the end region (3), and its tapering end extends as far as the outer edge (4) of the tablet. Since the tablet coat (5) material surrounding the core tablet (1) is interrupted at this position, an opening (6) is obtained through which active substance (2) can be released from the tablet.

Figure 2:
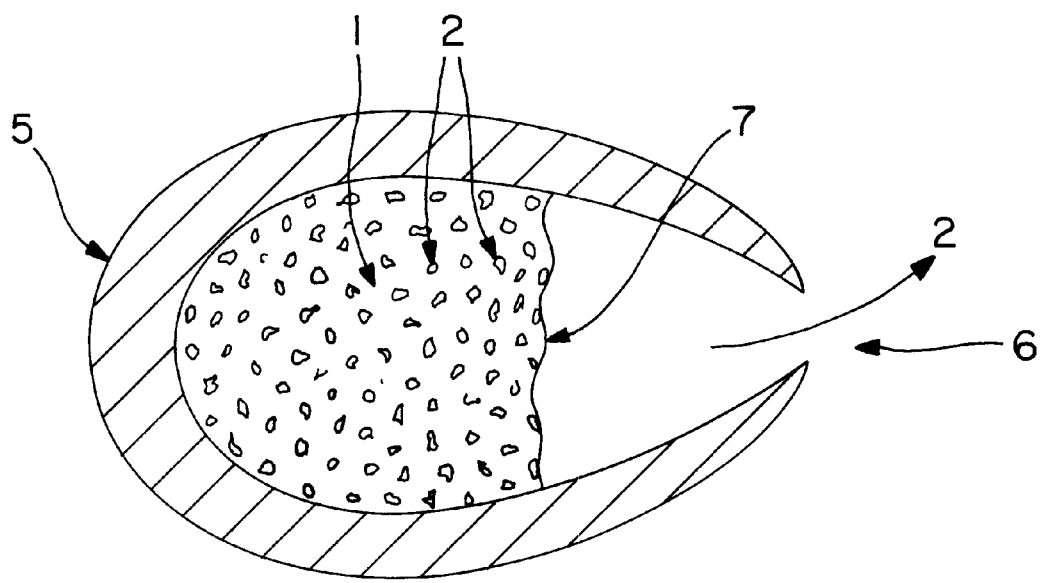
FIG. 2 illustrates a diffusion or erosion front as a result of release of active substance from the tablet of the present invention.

During the course of the release, which takes place either by diffusion from the core tablet (1) or by erosion of the core tablet (1), active substance (2) is first released from the end region (3) of the core tablet (1) lying at the outer edge (4) of the tablet. As a result of this, a diffusion or erosion front (7) is obtained which moves continuously away from the opening (6) and whose size, as shown in FIG. 2, is approximately identical to the cross-sectional area of the core tablet at its position. As the distance of the erosion front (7) from the opening (6) increases, which opening (6) remains approximately constant over the course of the release, the extent of the erodible surface increases, for example, on the basis of a function of first or second order, or else discontinuously.

The control over the rate of release is all the more effective, the more dimensionally stable the coat (5) is, at least over a substantial part of the duration of release, and the less permeable it is to the active substance. These conditions ensure that the release of active substance takes place predominantly at the position where the opening is located. Satisfying these conditions depends on the choice of auxiliaries and on the production parameters.

In principle, the coat (5) can be made up of physiologically compatible polymers, waxes, wax-like substances, fats, fatty acids, fatty alcohols or other pharmaceutically useful tabletting auxiliaries, if appropriate in mixture with further auxiliaries, for example antioxidants, colouring agents, pigments, flavouring agents, flow agents, release agents and lubricating agents, wetting agents, solubility enhancers, hydrophilizing agents, fillers, substances for adjusting the pH value, etc. Irrespective of the solubility of the material from which the coat (5) is made, the dissolution rate must be low so as to be able to ensure shape retention. The dissolution rate in turn depends not only on the solubility of the material, but also on the force with which the material is compressed. Even readily soluble materials can be pressed to provide a very slowly disintegrating coat if a correspondingly high press force is set. By contrast, substances used as disintegration accelerators in tabletting technology have an unfavorable effect on the shape retention of the coat (5). These disintegration accelerators are generally crosslinked, hydrophilic polymers with strongly swelling properties. Examples of these are crospovidone and croscarmellose.

Figure 3:
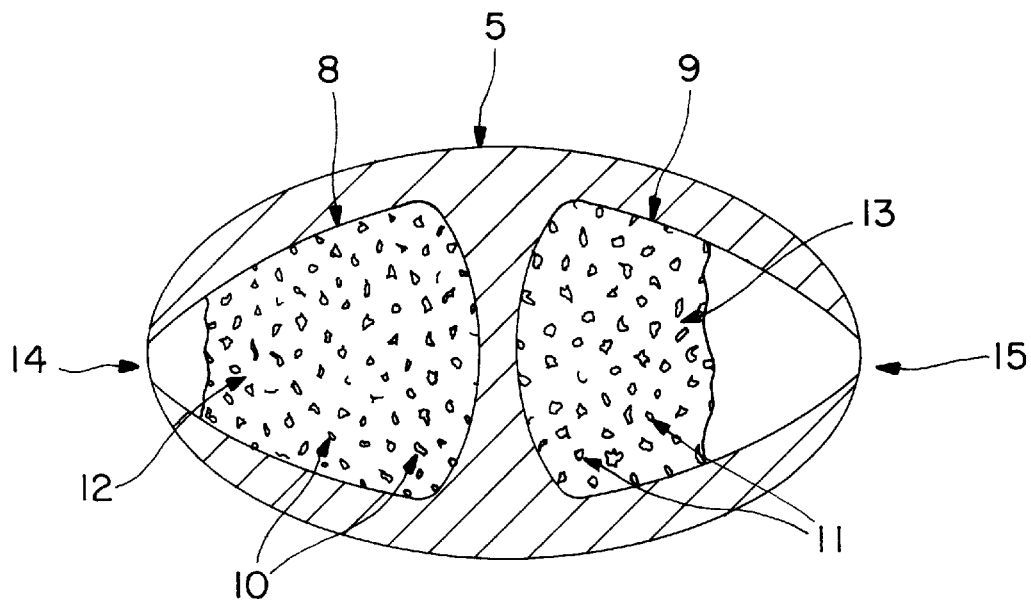

The invention also permits incorporation of more than one active substance. Thus, for example, it is possible, as is shown in FIG. 3, to incorporate two core tablets (8) and (9) with different active substances (10) and (11) in each tablet, their narrowing or tapering end regions (12) and (13) extending as far as the outer wall (4) of the tablet at different positions (14) and (15). Likewise, according to the invention, a tablet as in FIG. 1 can contain a core tablet (1) having more than one active substance (2). Finally, the tablet can also contain active substance in a zone such as in the coat (5), for example, or in an additionally introduced separate component, although this active substance is not then subject to the above-described mechanism of release control.

Limiting the size of the tablet to the minimum dimensions is particularly advantageous as regards administration. In general, efforts will at least be made to limit the size of the coat (5) by designing the latter thin in relation to the tablet diameter, and this can be assisted by matching the core shape to the tablet shape. It should be sought to limit the weight of the coat to at most 30% of the total weight of the tablet.

Figure 4:
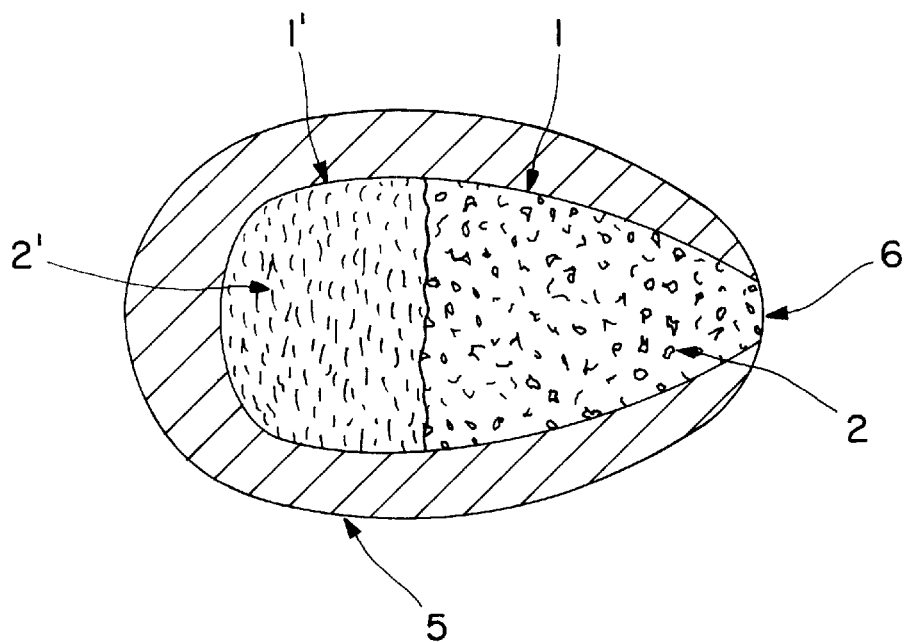

A tablet with a core tablet having two parts (1) and (1') is shown in FIG. 4. The core tablet parts (1, 1') contain different active substances (2) and (2'). These can be an active substance for pretreatment and then after-treatment of a medical condition, for example irritation of the mucous membrane of the stomach.

Tablets according to the invention are preferably produced by means of core tablets (1, 8, 9) containing active substance being first of all pressed from powder or granules on conventional tablet presses of the eccentric or rotatory type. These core tablets (1, 8, 9) are then transferred to a press for dry-coated tablets which is able to bring the core tablets very precisely into the desired position in die openings partially filled with powder or granules, and to press these with further powder or granules to give the dry-coated tablet. Presses designed for dry-coated tablets, and having the necessary precision as regards the transfer of core tablets, are described in DE 40 25 35 484, for example.

Although the main application area of the tablet according to the invention lies in the pharmaceutical sector, it can also be used very advantageously for controlled release of fertilizers and plant protection agents, since its prolonged duration of action obviates the work involved in the repeated application of conventionally dosed fertilizers and plant protection agents. The tablet can also be used advantageously for the release of anti-microbial substances, in particular in dishwashers and washing machines.

What is claimed is:

1. A method for producing a dry-coated tablet for the controlled release of an active substance, wherein said tablet comprises a core and a shell, wherein said core is shaped to have at least one tapered end and said shell has at least one opening, said at least one opening in the shell is located so that the opening is on the tapered end of said core, whereby a part of the tapered end of the core is uncovered by the shell, said core contains at least one active-substance containing material which is erodible in a liquid medium of application and said shell contains a material which is inherently stable in the liquid medium and which ensures that the release of the active substance takes place predominately through said opening, the erosion of the core by the liquid medium entering into the interior portion of the shell on application through said opening results in an erosion front area of the core increasing with application time and the erosion front correspondingly increases in distance from said opening with application time, said method comprising forming said core by compressing a powder or granules containing said active substance to form a shape having at least one tapered end;

feeding said core into a die opening of a compression coating machine, which has been previously partially filled with a powder or granules of the shell material, in such a way that the tapered end of said core extends to the wall of the die; and compressing said powder or granules of the shell material and said core together to yield a dry coated tablet which has a core and a shell, wherein said shell has an opening which does not cover the core.

2. A dry coated tablet for the controlled release of an active substance, comprising a compression molded core and shell, wherein said core is shaped to have at least one tapered end and said shell has at least one opening, said at least one opening in the shell is located so that the opening is on the tapered end of said core, whereby a part of the tapered end of the core is uncovered by the shell, wherein the core has a cross-section area which changes discontinuously as its distance from the opening in the shell increases, said core contains at least one active-substance containing material which is erodible in a liquid medium of application and said shell contains a material which is inherently stable in the liquid medium and which ensures that the release of the active substance takes place predominately through said opening, the erosion of the core by the liquid medium entering into the interior portion of the shell on application through said opening results in an erosion front area of the core increasing with application time and the erosion front correspondingly increases in distance from said opening with application time.

3. The tablet according to claim 2, wherein the shape of the dry-coated tablet corresponds to the shape of the core, and the core constitutes at least 70% of the weight of the tablet.

4. The tablet according to claim 2, wherein the core contains at least two different active substances and these are added either in homogeneous mixture or in different layers of the core.

5. The tablet according to claim 2, wherein the same or different active substance is additionally added to the shell material.

6. The tablet according to claim 2, which has at least two cores with different active substances in a polyfunctional dry-coated tablet.

7. The dry coated tablet according to claim 2, wherein the active substance comprises a pharmaceutically active substance.

8. A method for the oral administration of a pharmaceutically active substance which comprises orally administering to a patient a dry-coated tablet according to claim 7.

9. The dry coated tablet according to claim 2, wherein the active substance comprises a plant protective agent.

10. The dry coated tablet according to claim 2, wherein the active substance comprises a fertilizer.

11. The dry coated tablet according to claim 2, wherein the active substance comprises an anti-microbial agent.

* * * * *